United States Patent [19]

Scott et al.

[11] Patent Number: 5,383,928
[45] Date of Patent: Jan. 24, 1995

[54] STENT SHEATH FOR LOCAL DRUG DELIVERY

[75] Inventors: Neal A. Scott, Atlanta; Stephen R. Hanson, Stone Mountain; Spencer B. King, III; Laurence A. Harker, both of Atlanta, all of Ga.

[73] Assignee: Emory University, Atlanta, Ga.

[21] Appl. No.: 109,149

[22] Filed: Aug. 19, 1993

Related U.S. Application Data

[63] Continuation of Ser. No. 896,240, Jun. 10, 1992, abandoned.

[51] Int. Cl.⁶ .......................... A61F 2/06; A61F 2/04
[52] U.S. Cl. .......................... 623/1; 623/12; 606/194
[58] Field of Search .......................... 623/1, 11, 12; 606/191–200; 600/36

[56] References Cited

U.S. PATENT DOCUMENTS

| | | | |
|---|---|---|---|
| 4,687,482 | 8/1987 | Hanson | 623/12 |
| 4,776,337 | 10/1988 | Palmaz | 623/1 |
| 4,929,602 | 5/1990 | Harker et al. | 514/18 |
| 5,019,096 | 5/1991 | Fox, Jr. et al. | 623/1 |
| 5,037,378 | 8/1991 | Mueller et al. | 623/1 |
| 5,102,417 | 4/1992 | Palmaz | 606/195 |

FOREIGN PATENT DOCUMENTS

WO91/12779  9/1991  WIPO .

OTHER PUBLICATIONS

Murphy et al., "Polymeric Stents: Modern Alchemy or the Future?", *The Journal of Invasive Cardiology* 3:144–148 (1991).

Bailey et al., "Polymer Coating of Palmaz–Schatz Stent Attenuates Vascular Spasm After Stent Placement," *Circulation* 82:III-541 (1990).

Cavender et al., "The Effects of Heparin Bonded Tantalum Stents on Thrombosis and Neointimal Proliferation," *Circulation* 82:III-541 (1990).

van der Geissen et al., "Self-expandable Mesh Stents: An Experimental Study Comparing Polymer Coated and Uncoated Wallstent Stents in the Coronary Circulation of Pigs," *Circulation* 82:III-542 (1990).

*Primary Examiner*—David Isabella
*Assistant Examiner*—Debra S. Brittingham
*Attorney, Agent, or Firm*—Needle & Rosenberg

[57] ABSTRACT

This invention provides a sheath for encompassing at least a portion of a stent to locally deliver a drug to an arterial wall or lumen into which the stent has been inserted, comprising a polymer and a drug incorporated within the polymer, the polymer sheath encompassing at least a portion of the stent and a thickness to allow controlled release of the drug. Also provided is a method of preventing thrombosis and promoting and inhibiting vascular growth in a subject comprising inserting a stent encompassed by the sheath of the invention into a vessel of the subject.

25 Claims, 4 Drawing Sheets

STENT SHEATH FOR LOCAL DRUG DELIVERY

This application is a continuation of application Ser. No. 07/896,240, filed Jun. 10, 1992, now abandoned.

BACKGROUND OF THE INVENTION

In the United States and most other developed countries, the leading cause of mortality and morbidity is cardiovascular disease. Deaths from cardiovascular disease outnumber those from cancer by a factor of nearly two to one. Of those patients with cardiovascular-related diseases, coronary disease is the most important.

The heart, like any other tissue, requires a constant supply of blood in order to function properly. The blood supply to the heart is delivered through the coronary arteries. Patients with coronary artery disease usually have narrowings in one or several of these arteries. As a result, blood supply to the heart muscle is impaired. These narrowings are usually caused by deposits of fat, cholesterol, clotted blood and arterial tissue that calcify and harden over time (arteriosclerosis). If the supply of blood to the heart muscle is diminished below a certain level, then the heart muscle may initiate a series of responses that cause chest pain (angina). If the blood supply to an area of heart muscle is completely interrupted for a period of hours, then that area heart muscle will die (myocardial infarction or "heart attack").

Over the past several decades important developments have decreased the mortality and the suffering of millions of patients with coronary disease. The development of coronary artery bypass graft surgery (CABG) has proved to be useful in decreasing the incidence of coronary-related chest pain and, in selected cases, prolonging survival. In the late 1970's another method of mechanically increasing blood flow to the heart was developed. This technique is known as percutaneous transluminal coronary angioplasty (PTCA). A PTCA procedure is performed by placement of a catheter into an artery in the arm or leg. The catheter is then advanced to the coronary artery. A smaller catheter with a balloon near its tip is then advanced through the guide catheter and into the coronary artery. The angioplasty catheter is then placed into the obstruction and inflated. The pressure from the balloon is transmitted to the obstruction. This causes the artery to stretch and its inner lining to tear at the site. In addition, the narrowing is compressed against the artery wall. The balloon is then deflated and both catheters are removed. After allowing a period for the entry site in the arm or leg to heal (6–12 hours), the patient usually begins ambulating and may return to work after several days.

Although successful PTCA procedures produce a significant decrease in angina in selected patients, there are two major complications associated with this procedure: (1) acute occlusion of the vessel during or soon after the procedure, and (2) a process known as restenosis, where the vessel gradually narrows at the site of the PTCA.

The occurrence of acute occlusion at the angioplasty site is a serious complication and is the major contributor to the mortality and morbidity associated with PTCA. Acute occlusion of the vessel during or immediately after PTCA increases the procedure-related mortality five-fold when compared to occlusion-free patients. The myocardial infarction rates associated with acute occlusion are also significantly higher than in occlusion-free patients (27–56% versus 2%, respectively). Because of these complications, patients who experience an acute occlusion during an angioplasty procedure may undergo emergent coronary artery bypass grafting to restore myocardial blood flow. As expected, the mortality and incidence of myocardial infarction in patients who undergo emergent bypass grafting for acute closure are significantly higher than those of occlusion-free patients. Despite the experience gained since the early application of coronary angioplasty and improvements in catheter technology, the incidence of periprocedural acute closure has not changed in the period between two multicenter registry trials completed in 1981 and 1986. In addition, there has not been a significant change in the complications associated with acute closure.

Several studies have examined the coronary arteries of patients who died within several days of PTCA. These studies demonstrated that disruption and splitting of the atherosclerotic plaque, in addition to expansion of the vessel wall (particularly by the segment uninvolved by atherosclerosis) were the most likely causes for the improved angiographic appearance of the vessel. The investigators consistently found cracks and dissections between the intimal and medial layers at the junction of the plaque and the plaque-free segment of the arterial wall. These findings suggested that an uneven distribution of force existed between a rigid and somewhat non-expansile arteriosclerotic plaque and a more compliant less-arteriosclerotic area of the vessel wall. It was suggested that the lateral forces of the balloon induced tears at the junction of the two unequally elastic segments. These studies confirmed that the mechanism of PTCA was not due to compression and redistribution of the plaque but rather to extensive injury to the less arteriosclerotic segments of the artery. Variable degrees of intimal and medial plaque disruption occur during all PTCA procedures. Some lesions may demonstrate only mild, superficial splitting while others may display gross fissuring through the entire media and plaque mass, resulting in tears or dissections of the inner layers of the artery.

Although the exact cause of acute closure is unknown, the presence of large intimal tears or arterial dissections after PTCA has been consistently identified as a predictor of major ischemic complications. Although the angiographic detection of intimal disruption is somewhat insensitive, several studies have associated these tears and dissection with immediate vessel closure during PTCA. A reasonable assumption is that the intimal tears and dissections either directly occlude the artery or markedly disturb the flow patterns in the vessel and allow areas of blood stasis to form. Since non-flowing blood is very likely to clot, thrombus formation could begin in these areas of stasis and the thrombus may continue to grow until the vessel occludes.

Because of the serious complications associated with acute closure, several devices have been developed for use in this situation (Roubin et al., *Circulation* 81:92–100 (1990); Jenkins et al., *Circulation* 82:101–108 (1990); Stack et al., *Amer. J. Cardiol.* 61:77–80 (1988)). The device that appears to be most useful is the intracoronary stent. A stent is a device (usually made of metal) that can be placed in the artery at the site of the dissection. The use of intracoronary stents for the treatment of acute closure has markedly decreased the incidence of associated myocardial infarction and emergent coronary bypass surgery (Roubin et al., *Circulation* 83:916-927 (1992)). The proposed mechanism of action of intracoronary stents in the treatment of acute closure is the pinning of the intimal tears between the stent and the arterial wall, thereby maintaining vessel patency.

Although stents have been shown to be very effective in restoring vessel patency and decreasing myocardial ischemia, the exposure of the metal prosthetic surfaces to circulating blood initiates platelet and coagulation reactions that frequently result in thrombus formation and acute thrombotic occlusion of the stent. The occurrence of thrombosis at the stent site is a life-threatening emergency that usually results in an emergent coronary angioplasty or emergent coronary bypass surgery.

Because it is of utmost importance to avoid thrombosis of the stent and its serious complications, patients who receive stents are aggressively anticoagulated with heparin, aspirin, coumadin, dextran, and persantine. As expected, there is a high incidence of bleeding complications in these patients. A study performed at Emory University Hospital revealed that 33% of the patients who received stents for acute closure required transfusion and 7% of patients had an extremely large bleeding episode at the catheter entry site in the leg artery that necessitated surgical repair (Hearn et al., "Clinical and angiographic outcomes after coronary artery stenting for acute closure following percutaneous transluminal coronary angioplasty: initial results with a balloon-expandable, stainless steel design,"*J. Am. Coll. Cardiol.* (in press) (1992).

Because of the complications associated with systemic anticoagulation, extensive attempts have been made to design a stent that would be non-thrombogenic. A stent with little or no propensity to form thrombus would obviate or drastically decrease the need for aggressive anticoagulation. Initial stents were constructed of plastic. Because all of these stents thrombosed, stainless steel was then used. These stents appeared promising in canine peripheral arteries; however, most coronary stents used in clinical trials are composed of stainless steel and have a thrombotic occlusion rate of approximately 5-30%. Tantalum is another metal that is used in first-generation stents. Althrough initial reports of a lower thrombogenicity of tantalum stents appeared promising (van der Giessen et al., *Circulation* 80:II-173 (1989)), more careful study has shown that tantalum is as thrombogenic as stainless steel (de Jaegere et al., *Amer. J. Cardiol.* 69:598-602 (1992)).

The concept of coating a stent with a polymer has been described several years ago and is discussed in the literature regularly. In the past, local delivery of drug(s) using stents has centered around two concepts: (1) directly coating the stent wires with a drug or a drug-polymer combination (Bailey et al., *Circulation* 82:III--541 (1990); Cavendar et al., *Circulation* 82:III-541 (1990)) and (2) incorporating a drug into a stent that was constructed not of metal but of a biodegradable polymer (Murphy et al., *J. Invasive Cardiol.* 3:144-148 (1991)). Most investigators and stent companies have focused their efforts on directly coating the metal stent wires with a polymer. This polymer is usually placed directly on the stent (e.g., by dipping the stent in soluble polymer) or is covalently bound to the metal. The polymer is bonded to or contains an anticoagulant compound. Most coated stents currently under development use heparin as their active agent. One of the more effective polymer coatings for stents is Biogold (van der Giessen et al., *Circulation* 82:III-542 (1990)).

Unfortunately, Biogold and other coated stents have not completely prevented arterial thrombosis. This is probably related to the cracking of the polymer as the stent is expanded during deployment, saturation of the anticoagulant binding sites on the stent, and/or inadequacy of heparin as an anticoagulant in the prevention of arterial thrombosis.

Because of the inadequacies associated with polymer coatings directly applied onto the stent wires, there remains a great need to effectively prevent thrombosis at the stent site. The present invention satisfies this need by providing a separate sleeve to encompass the stent and serve as a local drug delivery device to prevent thrombosis.

In addition to thrombosis, restenosis is also a problem associated with angioplasty. Repeat coronary angiography usually reveals a significant stenosis at the PTCA site (i.e., restenosis). Usually these patients are left with a choice of repeat PTCA or coronary artery bypass surgery. There are approximately 300,000 coronary angioplasty procedures performed in this country annually. Since 30% of these procedures are complicated by restenosis, the development of an effective method to treat this problem would have an enormous impact on health care costs and the morbidity associated with PTCA.

In an attempt to prevent restenosis after PTCA, a large number of pharmacologic agents have been employed in clinical trials. Therapy with heparin, aspirin, coumadin, calcium channel blockers, thromboxane receptor antagonists, steroids, omega-3 fatty acids, and angiotensin converting enzyme inhibitors have failed to unequivocally prevent restenosis.

A porcine coronary balloon injury model has been developed in an attempt to find an animal model more representative of human post-angioplasty restenosis (Schwartz et al., *Circulation* 82:2190-2200 (1990); Karas et al, "Comparison of coronary intimal proliferation following balloon injury and stenting in swine: An animal model of restenosis," *J. Am. Coll. Cardiol.* (in press) (1992)). Morphologically and hemodynamically the porcine coronary vasculature is very similar to the human coronary system. Reproducible intimal proliferation is obtained after balloon injury of normal porcine coronary arteries. Histologically, the proliferative response to balloon injury in the pig coronary is very similar to the response seen in pathological studies of humans (Schwartz et al., *Circulation* 82:2190-2200 (1990)).

Thus, there is also a need to prevent restenosis following angioplasty. The present invention satisfies this need by providing a separate sleeve to encompass a stent to locally administer drugs to prevent restenosis.

SUMMARY OF THE INVENTION

This invention provides a sheath for encompassing at least a portion of a stent to locally deliver a drug to an arterial wall or lumen into which the stent has been inserted, comprising a polymer and a drug incorporated within the polymer, the polymer sheath encompassing at least a portion of the stent. The sheath also has a thickness to allow controlled release of the drug. Also provided is a method of preventing thrombosis and promoting and inhibiting vascular growth in a subject comprising inserting a stent encompassed by the sheath of the invention into a vessel of the subject.

DETAILED DESCRIPTION OF THE INVENTION

Figure 1:
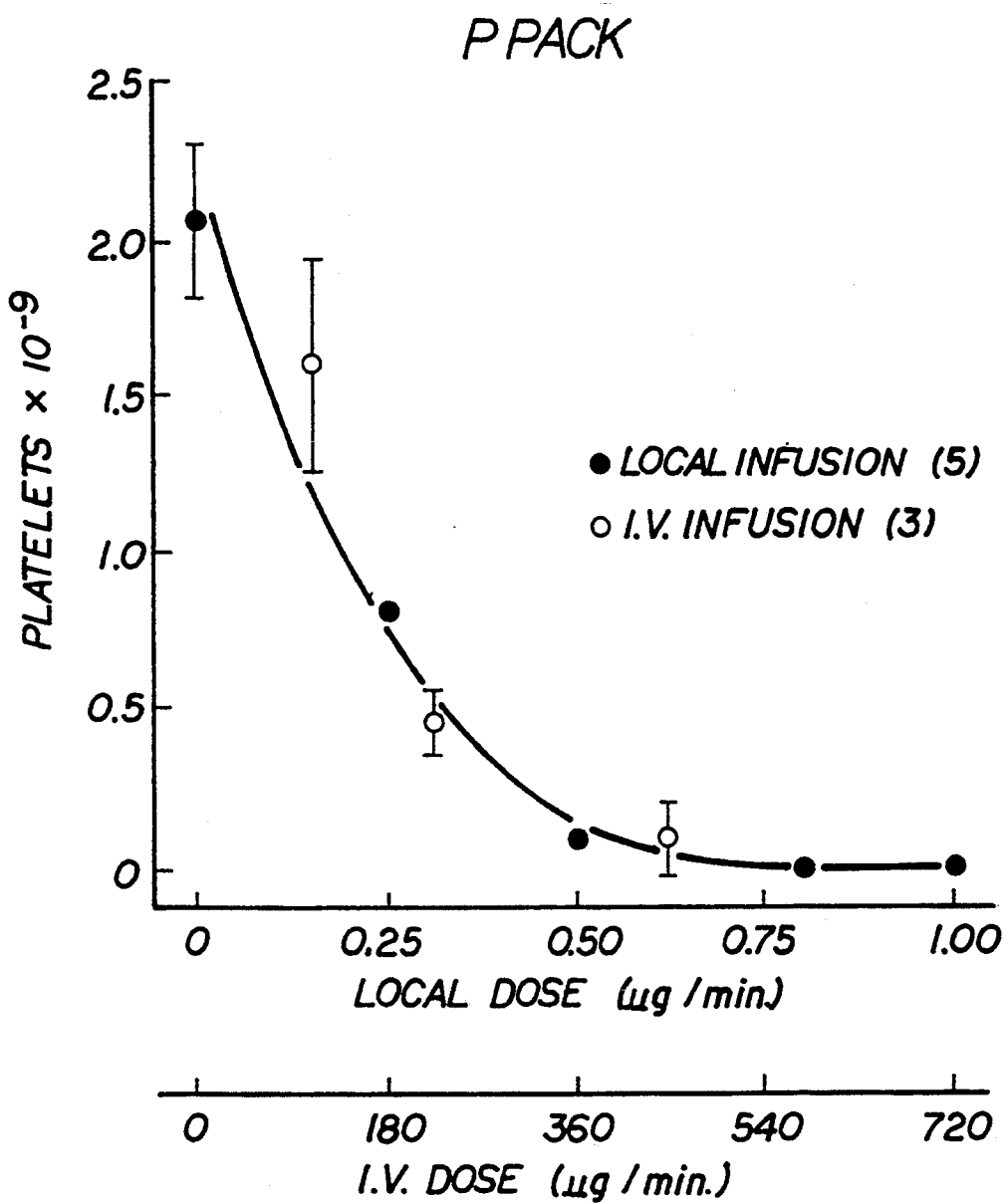
FIG. 1 shows a comparison of the dose-response curves of intravenous and local infusions of D-FPRCH2Cl for inhibition of platelet deposition on a Dacron vascular graft.

This invention provides a sheath for encompassing at least a portion of a stent to locally deliver a drug to an arterial wall or lumen into which the stent has been inserted. The sheath comprises a polymer and a drug incorporated within the polymer. The polymer sheath encompasses at least a portion of the stent and has a thickness sufficient to allow controlled release of the drug.

By "drug" is meant any compound which has a desired pharmacologic effect. Naturally, the drug is compatible with the polymer and can be tolerated in a subject. For example, the drug can be an anticoagulant, e.g., D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin, protaglandin inhibitors, platelet inhibitors, or tick anti-platelet peptide. The drug could also be a promoter of vascular cell growth, e.g., a growth factor inhibitor, growth factor receptor agonist, transcriptional activator, or translational promoter. Alternatively, the drug can be an inhibitor of vascular cell growth, e.g., a growth factor inhibitor, growth factor receptor antagonist, transcriptional repressor, translational repressor, antisense DNA, antisense RNA, replication inhibitor, inhibitory antibodies, antibodies directed against growth factors, bifunctional molecules consisting of a growth factor and a cytotoxin, bifunctional molecules consisting of an antibody and a cytotoxin. In addition, the drug could be a cholesterol-lowering agent, a vasodilating agent, and agents which interfere with endogenous vasoactive mechanisms. While the drug utilized in the specific example set forth herein is D-Phe-Pro-Arg chloromethyl ketone, these other compounds can be added to the polymer using very similar methods and routinely tested as set forth in the specification. Any modifications to the system necessary for a particular drug can routinely be made by one skilled in the art.

Many polymers can also be used to make the sheath, including biodegradable and non-degradable polymers. The polymer is selected depending on the drug selected, the polymer's compatibility with a subject and the ultimate pharmacologic effect desired. For example, if the effect need only last a short period, a thin polymer can be used with a limited amount of drug capable of diffusing from the polymer into the arterial wall or lumen. Alternatively, only the layer closest to the body fluid would contain the drug. Another alternative would be to use a polymer which is biodegradable over a short period of time. Naturally, the opposite characteristics would be selected for a desired prolonged release. The characteristics of the particular polymer for these purposes is well known to the skilled artisan or can be determined by reference to standard references, e.g., *Biodegradable Polymers as Drug Delivery Systems*, R. Langer and M. Chasin, Eds., Marcel Dekker Inc., New York, N.Y., USA (1990); Engleberg and Kohn, "Physico-mechanical properties of degradable polymers used in medical applications: a comparative study," *Biomaterials* 12:292–304 (1991); *Controlled Release Delivery Systems*, T. J. Roseman and S. D. Mansdorf, Eds., Marcel Dekker Inc., New York, N.Y., USA (1983); and "Controlled Release Technology, Pharmaceutical Applications, ACS Symposium Series, Vol. 348, P. I, Lee and W. R. Good, Eds., American Chemical Society, Washington, D.C., USA (1987).

Generally, the polymer has a drug release rate of between about 0.001 $\mu g/cm^2$-min and about 100 $\mu g/cm^2$-min, especially between about 0.01 $\mu g/cm^2$-min and 10 $\mu g/cm^2$-min. In addition, the polymer generally has a thickness of between about 0.01 mm and 10 mm, especially between about 0.1 mm and 1 mm.

As can be appreciated, the sheath can be comprised of two or more different drugs or two or more different polymers to obtain a desired effect and release rate. In addition, the polymers can have different solubilities or diffusion characteristics to accomplish non-uniform drug release. Finally, cultured or autologous cells can be used to line the sheath to achieve endothelialization.

Figure 3:
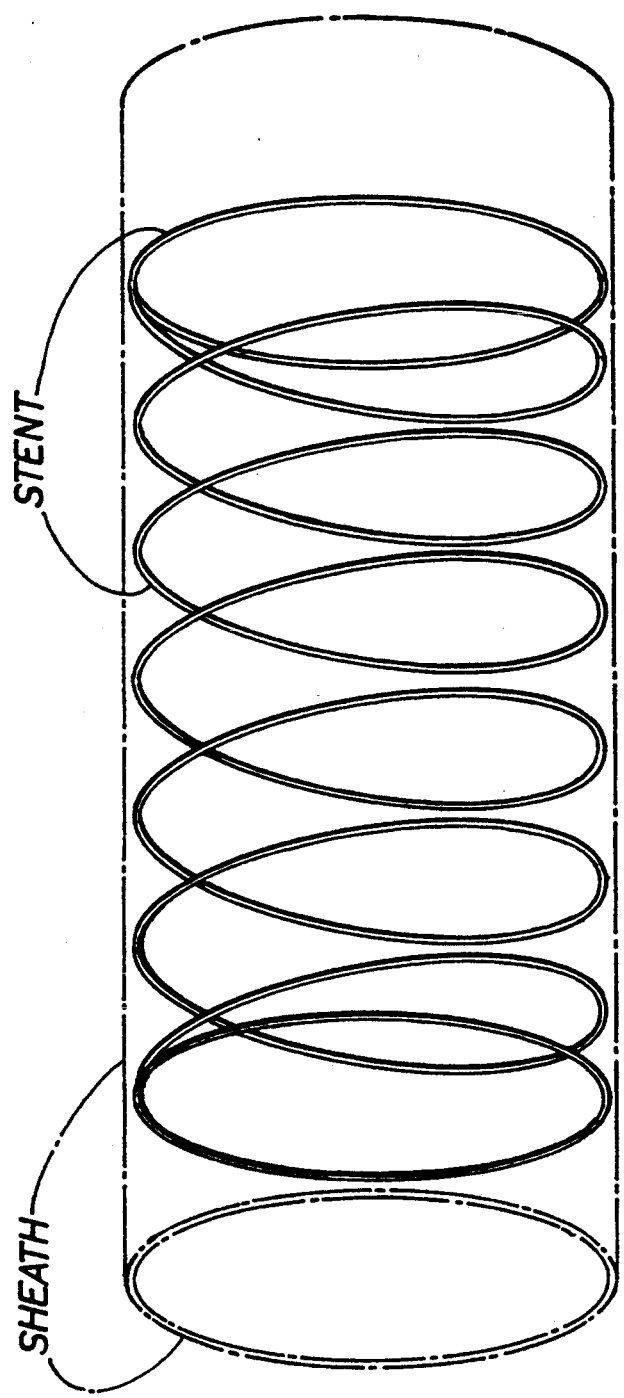
FIG. 3 shows a schematic drawing of the polymer sheath around a stent.

The invention also provides a kit comprising the sheath and a stent. Also disclosed is a device comprising a stent encompassed by the sheath. The initial prototype is a sleeve of polymer, either degradable or non-degradable, that covers the entire stent (FIG. 3). Modifications of the polymer coating include a ring that encompasses the proximal portion of the stent, single or multiple strips that cover a portion of the stent, or a polymer coating with perforations. Another use and design for the device is solely as a drug delivery agent deployed proximal to the targeted arterial segment. The device can have a much shorter length than a therapeutic stent.

Also disclosed is a method of preventing thrombosis in a subject comprising inserting a stent encompassed by the sheath into a vessel of the subject. In addition, a method of promoting vascular cell growth in a subject is provided comprising inserting a stent encompassed by a sheath containing a promoter of vascular growth into a vessel of a subject. Finally, the invention provides a method of inhibiting vascular cell growth in a subject comprising inserting a stent encompassed by a sheath containing an inhibitor of vascular cell growth into a vessel of the subject.

The polymer sheath apparatus allows for the delivery of drug(s) in a predictable manner since:

1. The maximal amount of drug delivered is that amount of drug incorporated into the polymer.

2. The duration of drug delivery is accurately predicted by the characteristics of the polymer. For example, if the polymer is biodegradable, then the rate and duration of drug delivery is related to the thickness of the polymer. If the polymer is not degradable, delivery is determined by the diffusion rate of drug through the polymer and the thickness of the polymer.

3. The kinetics of drug delivery is predicted by the solubility characteristics of the drug in the polymer. For example, if a drug is incorporated in a biodegradable polymer, a drug that is soluble in the polymer should have non-linear release rates, while a completely insoluble drug should be released in an approximately linear manner, which depends upon the rate of polymer degradation.

The utility of the polymer sheath is shown by calculations based on the concentration of locally infused compounds necessary to inhibit thrombosis. These calculations can be applied to other thrombosis inhibitors and other polymers to design alternative sleeves.

The invention demonstrates that D-FPRCH2Cl, 0.5 ug/min or an RGD peptide, 1 ug/min, infused 1 cm upstream of thrombogenic Dacron grafts (4 mm i.d. $\times$ 2 cm long = 2.5 $cm^2$) totally blocks thrombus formation (see FIGS. 1 and 2). We also found that drug concentrations when infused upstream are 20% of levels directly at the site of drug delivery. Therefore, for drug released from a film between the stent and the arterial wall, assuming a cylindrical surface, required release rates will be: D-FPRCH$_2$Cl: 0.5 ug/min / (2.5 $cm^2 \times 5$) and RGD: 1 ug/min/(2.5 $cm^2 \times 5$). Dividing the release rate for D-FPRCH$_2$Cl (0.04 ug/$cm^2$-min) by the density of solid drug (approximately 0.7 gm/$cm^3$), the rate of surface erosion is calculated as 0.8 microns per day for D-FPRCH$_2$Cl (and twice this value for an RGD peptide). For a polymer film 20% D-FPRCH$_2$Cl by volume, the erosion rate is 4 microns per day. Thus, a film 100 microns thick (0.1 mm) should protect for about 25 days (D-FPRCH$_2$Cl) or 12.5 days (RGD). At the very least, protection for several days can be achieved for many alternative sleeve formulations. Thus, the sleeves obviate the problems of acute thrombosis of the stent and bleeding due to systemic anticoagulation.

In the models discussed previously we have chosen to evaluate thrombin inhibitors other than D-FPRCH$_2$Cl because they are more specific inhibitors of thrombin, and are thus better suited to assess the role of thrombin in arterial thrombosis and cellular proliferation. In the initial studies, D-FPRCH$_2$Cl is appropriate for hypothesis testing, due to its potency and method of delivery, to determine whether more profound and global inhibition of coagulation proteases can be effective in this setting over a significant period of time. While D-FPRCH$_2$Cl is an alkylating agent, which may not ultimately be preferred, we have seen no toxicity in previous animal studies. Obviously, since preliminary studies with D-FPRCH$_2$Cl are successful, other antithrombins or heparins can be utilized.

Further, local delivery of growth factors or inhibitors by this method can be performed. For example, one can develop laminate films which deliver growth inhibitors abluminally, while delivering other agents luminally to anticoagulate the blood flow surface.

While the predictable release of a drug from the polymer sheath is a major improvement over current technology, an additional advantage is the drug sheath uses compounds in small amounts and therefore compounds that are much more potent than heparin in the prevention of thrombosis can be utilized. Alternative drug/sheath formulations can be easily tested following the formulations set forth above and the methods set forth below.

The following examples are intended to illustrate but not limit the invention. While they are typical of those that might be used, other procedures known to those skilled in the art may be alternatively employed.

EXPERIMENTAL METHODS

Figure 2:
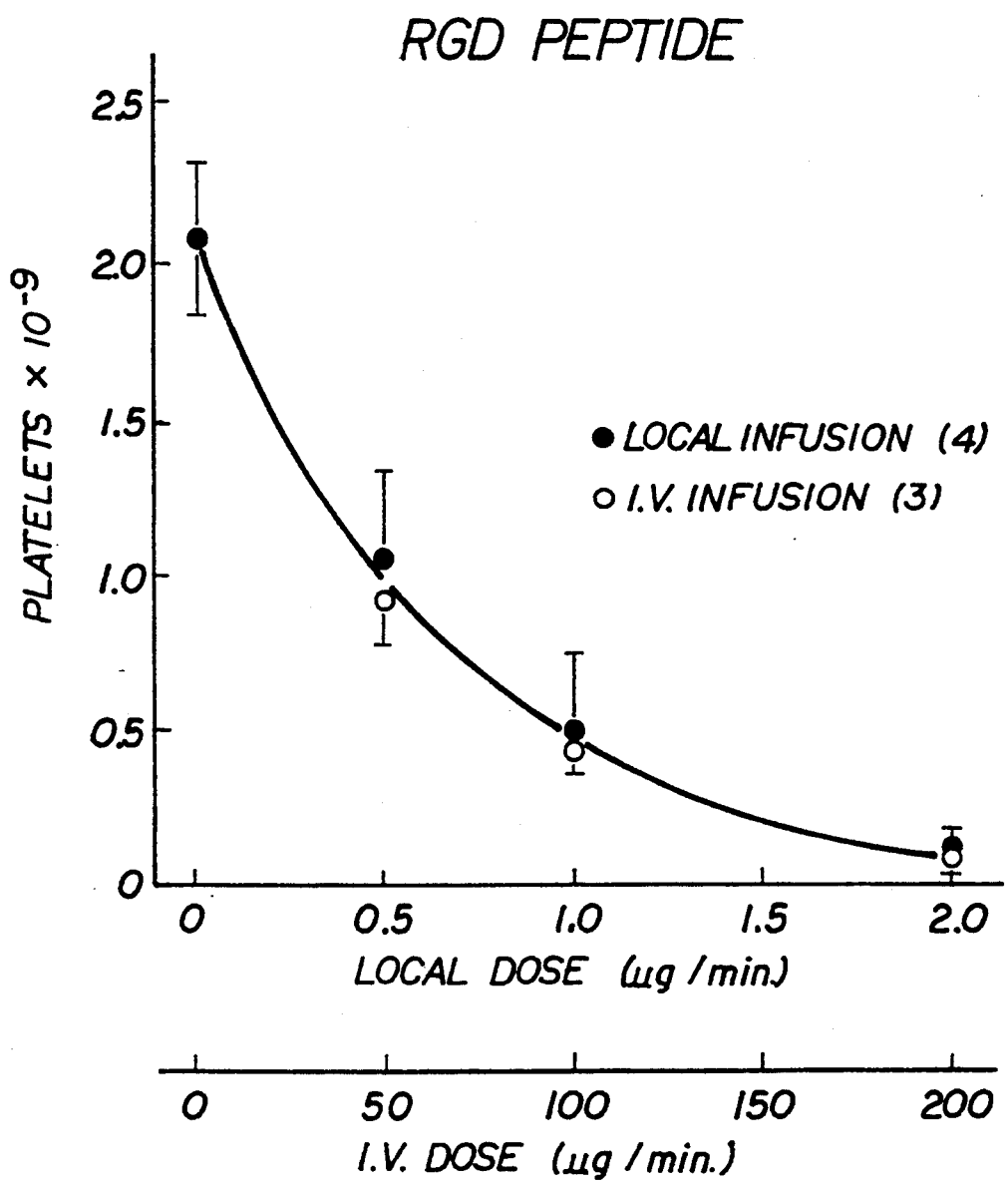
FIG. 2 shows a comparison of the dose-response curves of intravenous and local infusions of an RGD peptide for inhibition of platelet deposition on a Dacron vascular graft.

We examined the effect of local delivery of antithrombotic compounds on thrombus formation. We postulated that if the compound is delivered at or near the site of thrombus formation, very high local concentrations can be obtained with minimal or negligible systemic complications. We found that when the synthetic peptide D-Phe-Pro-Arg chloromethyl ketone (D-FPRCH$^2$Cl) which irreversibly alkylates the active site of thrombin is infused near the site of thrombus formation, the dose needed for complete inhibition of thrombosis is five hundred times less than the dose needed for an equivalent degree of inhibition with an intravenous D-FPRCH$^2$Cl infusion (FIG. 1). Similar data have been obtained for local infusion of an RGD peptide (FIG. 2). Preparation of films by solution casting Ethylene vinyl acetate copolymer (EVA), (Catalog #34,691-8) was obtained from Aldrich Chemical Company, Inc. (Milwaukee, Wis.). The mold used in casting these films (0.1–10 mm thickness) consisted of two square glass plates, (20 cm $\times$ 20 cm), with the top plate having a central circular hole (10.2 cm diameter). Both plates were cleaned with soap and sonicated in ethanol for 10 minutes. Once dry, the mold was placed in a glove-bag and leveled along each side. The films were prepared from 1.2 grams of polymer and 2.5% (weight/volume) solution in methylene chloride. The solution was filtered through a 0.45 micron membrane filter. The films were cast under a nitrogen atmosphere and left to dry overnight. They were then placed into petri dishes and stored under vacuum. Films are currently prepared using purified EVA. The films can be designed to contain a large variance of drug, generally, 5–30% by weight of drug.

Incorporation of D-FPRCH$_2$Cl into EVA films

EVA (264.3 mg) was dissolved in 10 ml of methylene chloride. The solution was filtered through a membrane filter and evaporated to 3 ml. While stirring the solution of EVA in methylene chloride, D-FPRCH$_2$Cl was added slowly. The EVA-D-FPRCH$_2$Cl suspension was poured into a pre-cooled circular glass mold in a glove box (nitrogen atmosphere). The mold was covered with filter paper to facilitate the slow evaporation of methylene chloride. The mold was removed from the glove box after two days and the film was carefully dried in high vacuum. After a total drying time of 3 days, the film was peeled from the mold and stored in a clean dish.

In vivo studies

Experimental Design: Animals and in vivo measurements of thrombus formation.

The films were placed to line the circumference of a 2 cm length of ePTFE grafts, over which a 2 cm long stent was deployed. Tantalum wound monofilament balloon expandable stents were used which have been provided by CORDIS, Inc., Miami Lakes, Fla. We have found these stents to be comparably thrombogenic to stainless steel stents of other manufacturers. Thrombus formation was assessed by $^{111}$In-platelet imaging as described (Hanson and Harker, "Interruption of acute platelet-dependent thrombosis by the synthetic antithrombin D-phenylalanyl-L-prolyl-Larginyl chloromethyl ketone," *Proc. Natl. Acad. Sci. USA* 85:3184–3188 (1988)). Briefly, chronic arteriorvenous shunts are surgically implanted between the femoral artery and vein in healthy male baboons. Blood flow through the shunt is established by connecting the two silicone rubber shunt segments. Thrombogenic segments (e.g., stents) may then be interposed between the segments of the permanent arteriovenous shunt. The extent of acute thrombus formation is measured in real time by scintillation camera imaging of autologous $^{111}$In platelets.

In addition, polymer-drug films which prevent thrombosis in the baboon and pig AV shunt system can be studied following stent-film placement in carotid, superficial femoral and coronary arteries following balloon injury of those vessels. Thrombus formation and its inhibition are documented at 3, 24, and 48 hours by platelet imaging of the carotid and femoral vessels according to methods described previously (Hanson et al., "Analysis of Indium-111 platelet kinetics and imaging in patients with aortic grafts and abdominal aortic aneurysms," *Arteriosclerosis* 10:1037–1044 (1990)) Briefly, $^{111}$In-platelet deposition is assessed with Gamma camera imaging in real time at intervals of 3, 24 and 48 hours after stent placement into either the carotid or femoral arteries. Platelet deposition on stents in carotid arteries is assessed by sacrificing the animal at one of the above time intervals. The heart is rapidly perfusion-fixed and the coronary segments containing the stent and a section of control artery are removed. Each segment is placed in a Gamma counter for determination of $^{111}$In-platelet deposition.

Male baboons weighing 8–12 kg, observed to be disease-free for 3 months were studied. Juvenile domestic swine of either sex weighing 20–35 kg were also studied. All procedures were approved by the Emory University Institutional Animal Care and Use Committees in accordance with federal guidelines (1990). The labeling of autologous platelets with $^{111}$In-oxine, and scintillation camera imaging were performed as described (Hanson and Harker, "Interruption of acute platelet-dependent thrombosis by the synthetic antithrombin D-phenylalanyl-L-prolyl-L-arginyl chloromethyl ketone," *Proc. Natl. Acad. Sci. USA* 85:3184–3188 (1988)). Briefly, animals had chronic arteriovenous shunts placed several days prior to the experiment. Platelets were labelled with $^{111}$Indium. At the time of the experiment, stents both with and without sheaths were placed in the arteriovenous shunt. The shunt containing the stent was then placed over a gamma camera. Platelet accumulation was calculated from the intensity of the $^{111}$In image of the stent on the gamma camera.

Results

Figure 4:
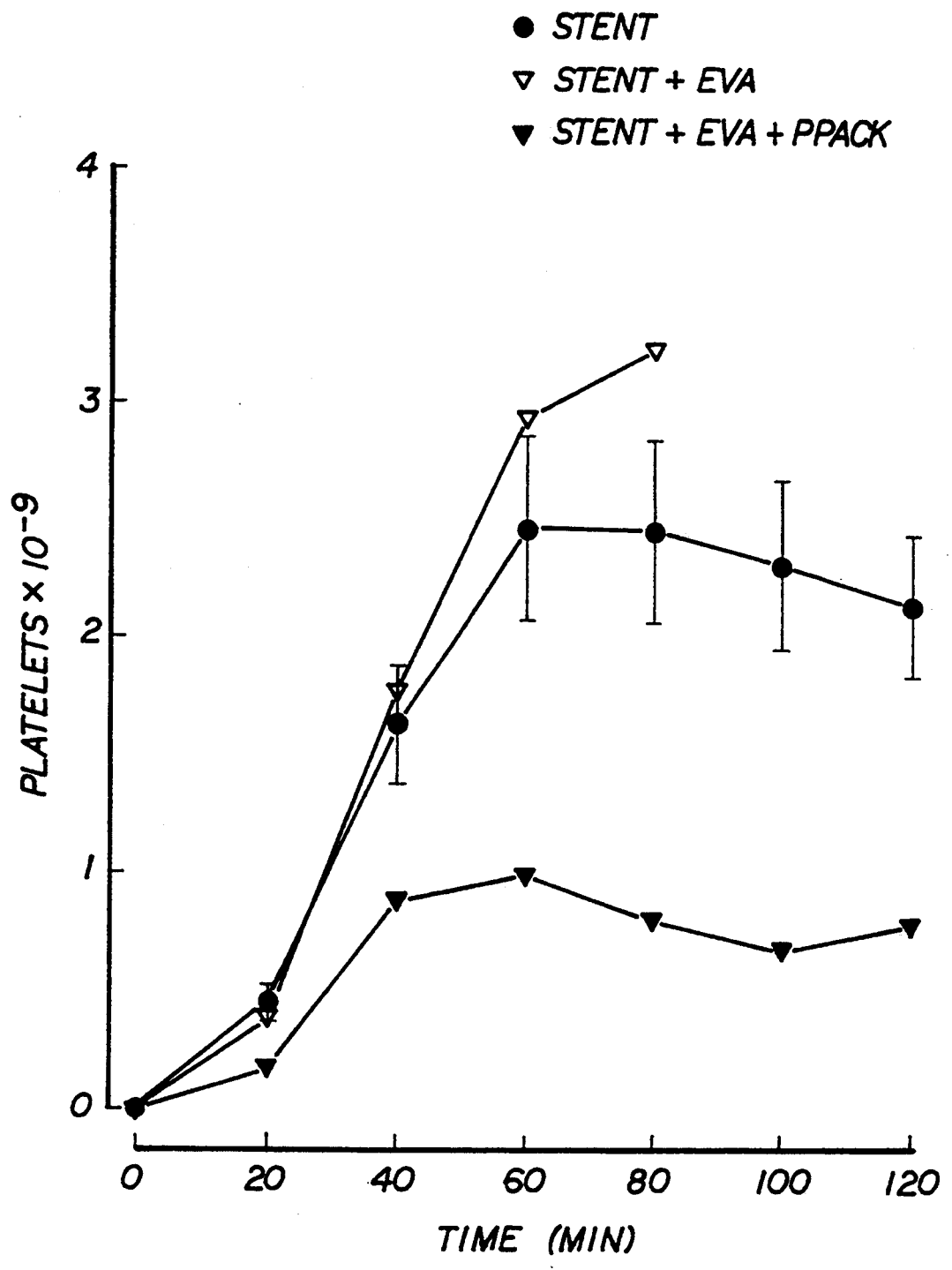
FIG. 4 shows platelet deposition on a polymer sheath covering a stent. Platelet deposition was measured with $^{111}$In-labelled platelets in a baboon arteriovenous shunt. The thrombogenicity of the stent alone (n=7) is depicted by the filled circles. The platelet deposition on a stent covered by an EVA polymer sheath was not significantly different from the stent alone (n=2). However, when the EVA polymer was filled with 5% D-FPRCH2Cl, there was a marked decrease in thrombogenicity.

Platelet deposition on the uncoated stents was similar to that seen with stainless steel stents from Cordis and other manufacturers. When the stents were combined with a polymer sheath made with 33% EVA, there was no significant change in thrombogenicity. However, when the stents were placed in the shunt in combination with an EVA polymer (33%) that contained approximately 5% D-FPRCH$_2$Cl, there was a significant reduction in platelet deposition (FIG. 4).

The concept of local delivery with a sleeve polymer-stent device has enormous therapeutic potential since the rate, concentration and duration of drug release can be accurately controlled. This method also allows for combinations of agents to be delivered. In addition, our sleeve device enables the targeting of drugs to be released not only into the lumen to prevent thrombosis, but also the release of drugs into the arterial wall to inhibit the cellular proliferative response.

Thus, a polymer sleeve device over a stent can deliver enough drug to inhibit thrombus formation. The experiment in FIG. 4 was performed with an EVA polymer containing only 5% D-FPRCH$_2$Cl. It is possible to load EVA and other polymers with approximately 30% D-FPRCH$_2$Cl. As described in the calculations, complete inhibition of thrombus formation at the stent site for over 3 week with this anticoagulant can be obtained.

Throughout this application various publications are referenced. The disclosures of these publications in their entireties are hereby incorporated by reference into this application in order to more fully describe the state of the art to which this invention pertains.

The preceding examples are intended to illustrate but not limit the invention. While they are typical of those that might be used, other procedures known to those skilled in the art may be alternatively employed.

What is claimed is:

1. In combination, a hollow tubular stent having a predetermined length and a separate sheath removably encompassing at least a portion of said hollow tubular stent to locally deliver at least one drug to an area selected from the group consisting of an arterial wall and an arterial lumen into which the stent has been inserted, comprising at least one polymer and at least one drug incorporated within the polymer, the sheath removably encompassing at least a portion of the stent and having a thickness to allow controlled release of the drug.

2. The sheath of claim 1, wherein the drug is an anticoagulant.

3. The sheath of claim 2, wherein the anticoagulant is D-Phe-Pro-Arg chloromethyl ketone.

4. The sheath of claim 2, wherein the anticoagulant is selected from the group consisting of an RGD peptide-containing compound, heparin, antithrombin compounds, platelet receptor antagonists, anti-thrombin antibodies, anti-platelet receptor antibodies, aspirin, protaglandin inhibitors, platelet inhibitors and tick anti-platelet peptide.

5. A method of preventing thrombosis in a subject comprising inserting a stent encompassed by the sheath of claim 2 into a vessel of the subject.

6. The sheath of claim 1, wherein the drug is a promoter of vascular cell growth.

7. The sheath of claim 6, wherein the promoter of vascular cell growth is selected from the group consisting of a growth factor inhibitor, growth factor receptor agonist, transcriptional activator, translational promoter.

8. A method of promoting vascular cell growth in a subject comprising inserting a stent encompassed by the sheath of claim 6 into a vessel of a subject.

9. The sheath of claim 1, wherein the drug is an inhibitor of vascular cell growth.

10. The sheath of claim 9, wherein the inhibitor of vascular cell growth is selected from the group consisting of a growth factor inhibitor, growth factor receptor antagonist, transcriptional repressor, translational repressor, antisense DNA, antisense RNA, replication inhibitor, inhibitory antibodies, antibodies directed against growth factors, bifunctional molecules consisting of a growth factor and a cytotoxin, bifunctional molecules consisting of an antibody and a cytotoxin.

11. A method of inhibiting vascular cell growth in a subject comprising inserting a stent encompassed by the sheath of claim 9 into a vessel of the subject.

12. The sheath of claim 1, wherein the drug is selected from the group consisting of a cholesterol-lowering agent, a vasodilating agent, and agents which interfere with endogenous vasoactive mechanisms.

13. The sheath of claim 1, wherein the polymer is nondegradable.

14. The sheath of claim 1, wherein the polymer is biodegradable.

15. The sheath of claim 1, wherein the polymer has a drug release rate of between about 0.001 $\mu g/cm^2$-min and about 100 $\mu g/cm^2$-min.

16. The sheath of claim 1, wherein the thickness of the polymer is between about 0.01 mm and 10 mm.

17. The sheath of claim 1, wherein the thickness of the polymer is between about 0.1 mm and 1 mm.

18. The sheath of claim 1, wherein the sheath is comprised of at least two different drugs.

19. The sheath of claim 1, wherein the sheath is comprised of at least two different polymers.

20. The sheath of claim 19, wherein the polymers have different solubilities.

21. The sheath of claim 19, wherein the polymers have different diffusion characteristics.

22. The sheath of claim 1, further comprising cultured or autologous cells which line the sheath.

23. The device of claim 1, wherein the sheath removably encompasses the entire sheath.

24. The device of claim 1, wherein the sheath removably encompasses only the proximal end of the stent.

25. A kit comprising a hollow tubular stent and a separate sheath for removably encompassing at least a portion of the stent to locally deliver at least one drug to an area selected from the group consisting of an arterial wall and an arterial lumen into which the stent has been inserted, comprising at least one polymer and at least one drug incorporated within the polymer, the sheath removably encompassing at least a portion of the stent and having a thickness to allow Controlled release of the drug.

* * * * *